| United States Patent [19] | [11] | 4,299,830 |
|---|---|---|
| Gubitz | [45] | Nov. 10, 1981 |

[54] 1,5-METHANO-1,4-BENZODIAZOCINES, INTERMEDIATES THEREFOR, AND METHOD OF USE AND COMPOSITIONS THEREOF

[75] Inventor: Franklyn W. Gubitz, Nassau, N.Y.

[73] Assignee: Sterling Drug Inc., New York, N.Y.

[21] Appl. No.: 161,280

[22] Filed: Jun. 20, 1980

[51] Int. Cl.$^3$ .................. C07D 471/08; A61K 31/495
[52] U.S. Cl. .................................... 424/250; 544/344
[58] Field of Search ......................... 544/344; 424/250

[56] References Cited

U.S. PATENT DOCUMENTS 3,472,852  10/1969  Gutitz ................................. 544/344

FOREIGN PATENT DOCUMENTS 41-13031  7/1966  Japan .................................. 544/344

*Primary Examiner*—Mark L. Berch

*Attorney, Agent, or Firm*—Theodore C. Miller; B. Woodrow Wyatt

[57] ABSTRACT

4-Q-9-RR'N-3,4,5,6-tetrahydro-2H-1,5-methano-1,4-benzodiazocines wherein

Q is propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl; and R and R' are both hydrogens or both methyls; or R is hydrogen and R' is methyl, ethyl, propyl, butyl, isobutyl or benzyl and acid addition salts thereof are useful as strong analgesics and are prepared from the known 3,4,5,6-tetrahydro-2H-1,5-methano-1,4-benzodiazocine by multi-step processes including acylation (including acetylation), nitration, nitro reduction, amide reduction, deacetylation, alkylation and dimethylation.

20 Claims, No Drawings

1,5-METHANO-1,4-BENZODIAZOCINES, INTERMEDIATES THEREFOR, AND METHOD OF USE AND COMPOSITIONS THEREOF

BACKGROUND OF THE INVENTION

1. Field of the Invention

The invention relates to 4-alkylated-9-aminated-3,4,5,6-tetrahydro-2H-1,5-methano-1,4-benzodiazocines, intermediates therefor, and processes for preparation, method of use and compositions thereof.

2. Description of the Prior Art

Gubitz U.S. Pat. No. 3,472,852 describes 1,2,3,4,5,6-hexahydro-4-(RCH$_2$)-1,5-methano[g][1,4]diazocines having the structural formula

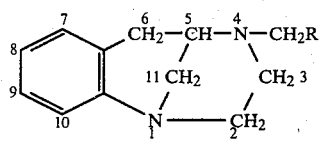

Formula A wherein R is hydrogen, lower-alkyl, lower-alkenyl, cyclopropyl or benzyl and having utility as "antagonists of certain strong analgesic agents, such as morphine and meperidine".

SUMMARY OF THE INVENTION

In a first composition of matter aspect the invention is 4-Q-9-RR'N-3,4,5,6-tetrahydro-2H-1,5-methano-1,4-benzodiazocine having the structural formula

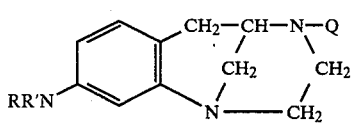

Formula I wherein
Q is propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl; and
R and R' are both hydrogens or both methyls; or
R is hydrogen and R' is methyl, ethyl, propyl, butyl, isobutyl or benzyl; or
an acid addition salt thereof.

The compounds of Formula I are useful as strong analgesics.

In a second composition of matter aspect the invention is 4-Q'-9-amino-3,4,5,6-tetrahydro-2H-1,5-methano-1,4-benzodiazocine having the structural formula

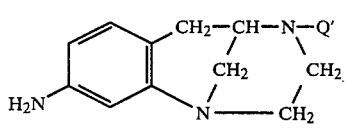

Formula II wherein
Q' is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl; or
an acid addition salt thereof.

In a third composition of matter aspect the invention is 4-Q'-9-nitro-3,4,5,6-tetrahydro-2H-1,5-methano-1,4-benzodiazocine having the structural formula

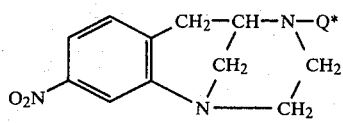

Formula III wherein Q* is hydrogen, acetyl or Q', wherein Q' has the same meanings ascribed thereto in Formula II or an acid addition salt thereof.

In a fourth composition of matter aspect the invention is 4-Q-9-nitro-3,4,5,6-tetrahydro-2H-1,5-methano-1,4-benzodiazocine having the structural formula

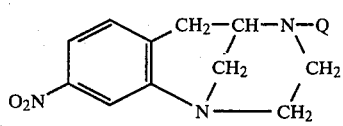

Formula IV wherein Q has the same meanings ascribed thereto in Formula I or an acid addition salt thereof.

In a fifth composition of matter aspect the invention is 4-Q-9-R"CONH—3,4,5,6-tetrahydro-2H-1,5-methano-1,4-benzodiazocine having the structural formula

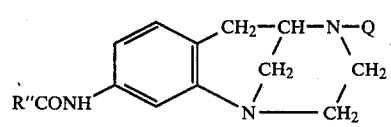

Formula V wherein
Q has the same meanings ascribed thereto in Formula I; and
R"CONH is formamido, acetamido, propionamido, butyramido, isobutyramido or benzamido; or
an acid addition salt thereof.

In a sixth composition of matter aspect the invention is 4-Q'-9-R"CONH—3,4,5,6-tetrahydro-2H-1,5-methano-1,4-benzodiazocine having the structural formula

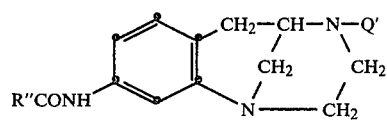

Formula VI wherein Q' has the same meanings ascribed thereto in Formula II and R"CONH has the same meanings ascribed thereto in Formula V or an acid addition salt thereof.

The compounds of Formulas II-VI are useful as intermediates for preparing the compounds of Formula I.

In a first process aspect the invention is the process of preparing a compound of Formula I wherein R and R' are both hydrogens or an acid addition salt thereof which comprises:

nitrating the corresponding 4-Q'-3,4,5,6-tetrahydro-2H-1,5-methano-1,4-benzodiazocine having the structural formula

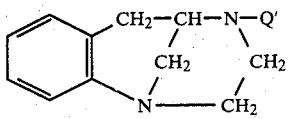

Formula VII wherein Q' has the same meanings ascribed thereto in Formula II or an acid addition salt thereof to form the corresponding compound of Formula III or an acid addition salt thereof; and then
reducing the corresponding compound of
Formula III or an acid addition salt thereof to form the corresponding compound of Formula II or an acid addition salt thereof; and then
reducing the corresponding compound of Formula II or an acid addition salt thereof.

In a second process aspect the invention is the process of preparing a compound of Formula I wherein R and R' are both hydrogens or an acid addition salt thereof which comprises:
nitrating 4-acetyl-3,4,5,6-tetrahydro-2H-1,5-methano-1,4-benzodiazocine having the structural formula

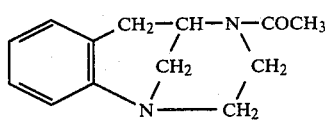

Formula VIII or an acid addition salt thereof to form the compound of Formula III wherein
Q* is acetyl or an acid addition salt thereof; and then
hydrolyzing the compound of Formula III wherein Q* is acetyl or an acid addition salt thereof to form the compound of Formula III wherein Q* is hydrogen or an acid addition salt thereof; and then
alkylating the compound of Formula III wherein Q* is hydrogen or an acid addition salt thereof with Q-An wherein An is the anionic part of a strong organic or inorganic acid to form a compound of Formula IV or an acid addition salt thereof; and then
reducing the compound of Formula IV or an acid addition salt thereof.

In a third process aspect the invention is the process of preparing a compound of Formula I wherein R and R' are both hydrogens or an acid addition salt thereof which comprises:
nitrating the corresponding 4-Q-3,4,5,6-tetrahydro-2H-1,5-methano-1,4-benzodiazocine having the structural formula

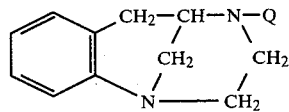

Formula IX wherein
Q has the same meanings ascribed thereto in Formula I or an acid addition salt thereof to form the corresponding compound of Formula IV or an acid addition salt thereof; and then
reducing the corresponding compound of Formula IV or an acid addition salt thereof.

In a fourth process aspect the invention is the process of preparing a compound of Formula I wherein R and R' are both methyls or an acid addition salt thereof which comprises dimethylating the corresponding compound of Formula I wherein R and R' are both hydrogens or an acid addition salt thereof.

In a fifth process aspect the invention is the process of preparing a compound of Formula I wherein R is hydrogen and R' is methyl, ethyl, propyl, butyl, isobutyl or benzyl or an acid addition salt thereof which comprises:
acylating the corresponding compound of Formula I wherein R and R' are both hydrogens or an acid addition salt thereof with an acid halide or acid anhydride of formic acid, acetic acid, propionic acid, butyric acid, isobutyric acid or benzoic acid to form the corresponding compound of Formula V or an acid addition salt thereof; and then
reducing the corresponding compound of Formula V or an acid addition salt thereof.

In a sixth process aspect the invention is the process of preparing a compound of Formula I wherein R is hydrogen and R' is methyl, ethyl, propyl, butyl, isobutyl or benzyl or an acid addition salt thereof which comprises:
acylating the corresponding compound of Formula II wherein R and R' are both hydrogens or an acid addition salt thereof with an acid halide or acid anhydride of formic acid, acetic acid, propionic acid, butyric acid, isobutyric acid or benzoic acid to form the corresponding compound of Formula VI or an acid addition salt thereof; and then
reducing the corresponding compound of Formula VI or an acid addition salt thereof.

In a method of use aspect the invention is the process of producing analgesia in a mammal in pain which comprises administering to the mammal an analgesically effective amount of a compound of Formula I or an acid addition salt thereof.

In a composition aspect the invention is a pharmaceutical composition in solid or liquid dosage form for oral or parenteral administration consisting essentially of a compound of Formula I or a pharmaceutically acceptable acid addition salt thereof and a pharmaceutically acceptable vehicle.

DETAILED DESCRIPTION OF THE INVENTION INCLUSIVE OF THE PREFERRED EMBODIMENTS

Preparation of the Compounds

The compounds of Formula VII, VIII and IX and acid addition salts thereof are generally known and are prepared by the methods described in above-cited Gubitz U.S. Pat. No. 3,472,852.

The nitration steps of the first, second and third process aspects of the invention are accomplished with nitric acid or a metal salt thereof in a strongly acidic solvent or solvent mixture. The metal salts of nitric acid can include the alkali metal, alkaline earth metal and transition metal salts. The strongly acidic solvents include the strong inorganic acids, especially sulfuric acid and the strong organic acids, for example acetic acid, and anhydrides thereof, for example acetic anhydride. Nitric acid itself is a strong acid and forms from the strongly acidic solvent when a metal salt of nitric acid is used. Generally, the strong acid or strong acid mixture itself serves as the solvent. Water is generally present in small amounts. Nitration temperatures in the range from $-50°$ C. to $150°$ C. can be used, and temperatures in the range from 0° C. to 100° C. are preferred. Generally, to avoid too rapid reaction, the nitric acid or metal salt thereof is added cautiously at about 25° C. or less.

The nitro reduction steps of the first, second and third process aspects of the invention are accomplished by any method effective in reducing nitro to amino without otherwise reducing or transforming the molecule. Numerous such methods are known as shown by R.O.C. Norman "Principles of Organic Synthesis" (Methuen & Co. Ltd., London, 1968, pp. 578–580) and Calvin A. Buehler and Donald E. Pearson "Survey of Organic Synthesis" (Wiley-Interscience, New York, 1970, pp. 413–417). Two general methods are chemical reduction with a metal and a mineral acid and catalytic reduction with hydrogen and a metal catalyst. Chemical reduction with iron and hydrochloric acid and catalytic reduction with hydrogen and palladium on carbon under pressure are particularly preferred. In the chemical reduction the mineral acid serves as solvent. A co-solvent or a mixture thereof can also be used, for example an acid, particularly acetic acid or an alcohol, particularly ethanol or a mixture thereof. Reduction temperatures in the range from −50° C. to 150° C. can be used, and temperatures in the range from 0° C. to 100° C. are preferred.

The amido carbonyl reduction steps of the first, fifth and sixth process aspects of the invention are accomplished by any method effective in reducing carbonyl to methylene without otherwise reducing or transforming the molecule. Several such methods are known ("Survey of Organic Synthesis", ibid., pp. 421–423), the most important of which is metal hydride reduction, especially with lithium aluminum hydride but also with diborane. An ethereal solvent, for example tetrahydrofuran, is generally used. Reduction temperatures in the range from −50° C. to 150° C. can be used, and temperatures in the range from 0° C. to 100° C. are preferred.

The hydrolysis step of the second process aspect of the invention is accomplished with aqueous mineral acid, for example hydrochloric acid or sulfuric acid, at a temperature in the range from 50° C. to 150° C.

The alkylation step of the second process aspect of the invention is accomplished with Q-An in the presence of an acid absorber, wherein An is the anionic part of a strong organic or inorganic acid which is a good leaving group and which does not interfere with the alkylation, especially halide, for example chloride or bromide, or arylsulfonate, for example, p-toluenesulfonate. Any effective acid absorber can be used, especially an alkali metal bicarbonate, for example, sodium bicarbonate. Ordinarily it is preferable to use a diluent such as a lower alkanol, for example methanol or ethanol, or an N,N-(di-lower-alkyl)-lower-alkanamide, for example N,N-dimethylformamide or N,N-dimethylacetamide. The alkylation can be carried out at a temperature in the range from −50° C. to 150° C. preferably from 0° C. to 100° C.

The fourth process aspect of the invention is best accomplished by reductive amination with formaldehyde by chemical reduction with formic acid or by catalytic reduction with hydrogen and a metal catalyst, for example palladium on carbon, under pressure. An inert hydrophilic solvent selected from the alcohols, for example ethanol, and ethers, for example, tetrahydrofuran, and water itself or a mixture thereof can be used. Reduction temperatures in the range from −50° C. to 150° C. can be used, and temperatures in the range from 0° C. to 100° C. are preferred.

The acylation step of the fifth and sixth process aspects of the invention is accomplished using the acid halide or acid anhydride itself as solvent or in combination with an inert solvent, for example pyridine or tetrahydrofuran, or a mixture of such solvents at a temperature in the range from −50° C. to 150° C., preferably from 0° C. to 100° C.

Since the compounds of Formulas I-IX are synthetic, they are racemic and can be resolved into their optical isomers by conventional methods.

The compounds of Formulas I—IX are amino bases and react with organic and inorganic acids to form acid addition salts. Due to the presence of the basic amino grouping, the free base forms represented by the formulas react with organic and inorganic acids to form acid addition salts. The acid addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid addition salt is isolated by filtration, if it is insoluble in the reaction medium, or by evaporation of the reaction medium to leave the acid addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, mandelic acid, cholic acid, 2-pyridinecarboxylic acid, pamoic acid, 3-hydroxy-2-naphtholic acid, picric acid, quinic acid, tropic acid, 3-indoleacetic acid barbituric acid, sulfamic acid, methanesulfonic acid, ethanesulfonic acid, isethionic acid, benzenesulfonic acid, p-toluenesulfonic acid, naphthalene-2-sulfonic acid, naphthalene-2,5-disulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like. All of the acid addition salts are useful as sources of the free bases by reaction with a stronger base. Thus, if one or more characteristics such as solubility, molecular weight, physical appearance, toxicity or the like of a given base or acid addition salt thereof render that form unsuitable for the purpose at hand, it can be readily converted to another, more suitable form. For pharmaceutical purposes, acid addition salts of relatively non-toxic, pharmaceutically-acceptable acids, for example hydrochloric acid, lactic acid, tartaric acid, and the like, are of course employed. Either the free bases or the acid addition salts thereof may crystallize as crystalline solvates with solvent of crystallization in integral or fractional amounts, for example, as the hydrate, sesquihydrate or ethanolate.

The following examples illustrate the invention. Structures of compounds are inferred from reaction types. Confirmations of structures are made by analyses of the elements, ultraviolet spectra, infrared spectra, nuclear magnetic resonance spectra and/or mass spectra. Courses of reactions and homogeneities of products are ascertained by thin layer chromatography and/or gas-liquid chromatography. Melting and boiling points or ranges are uncorrected unless otherwise indicated.

EXAMPLE 1

A. A mixture of 3,4,5,6-tetrahydro-2H-1,5-methano-1,4-benzodiazocine (described as 1,2,3,4,5,6-hexahydro-1,5-methanobenzo[g][1,4]diazocine by Gubitz U.S. Pat. No. 3,472,852) (5.63 g.) and cyclopropanecarboxylic acid anhydride in excess was heated on a steam bath for two hours. Methanol in excess was added, heating was continued, and the volatiles were boiled off, first at atmospheric pressure and then under vacuum. A chloroform solution of the residue was washed with aqueous potassium carbonate (10%), dried over potassium carbonate, treated with charcoal, filtered and stripped of solvent. Distillation of the residue under vacuum afforded 4-cyclopropanecarbonyl-3,4,5,6-tetrahydro-2H-1,5-methano-1,4-benzodiazocine (6.6 g., b.r. 160°-165° C./0.03 mm), the compound of Formula VII wherein Q' is cyclopropanecarbonyl.

B. Potassium nitrate (3.53 g.) was added in portions at room temperature to a solution of 4-cyclopropanecarbonyl-3,4,5,6-tetrahydro-2H-1,5-methano-1,4-benzodiazocine (7.07 g.) in concentrated sulfuric acid (about 25 ml.). The solution was heated, then stirred overnight, then quenched in ice (about 250 ml.). The resulting mixture was basified with aqueous sodium hydroxide (35%). After addition of solid potassium carbonate and sodium sulfate the mixture was extracted twice with chloroform. The combined chloroform extracts were dried over potassium carbonate, filtered and stripped of chloroform. Ethanolic hydrochloric acid, then ester, were added to a solution of the resulting orange glass (9.4 g.) in isopropyl alcohol. Recrystallization of the resulting solid from isopropyl alcohol-methanol afforded 4-cyclopropanecarbonyl-9-nitro-3,4,5,6-tetrahydro-2H-1,5-methano-1,4-benzodiazocine hydrochloride (6.57 g., m.r. 197°-204° C.), all but 2.2 g. of which was converted to the free base with aqueous sodium hydroxide. Crystallization of the free base from isopropyl alcohol-isopropyl acetate-ether afforded 4-cyclopropanecarbonyl-9-nitro-3,4,5,6-tetrahydro-2H-1,5-methano-1,4-benzodiazocine (1.64 g., m.r. 97°-99° C.), the compound of Formula III wherein Q' is cyclopropanecarbonyl.

C. Iron powder (104 g.) was added to a warm (50° C.) solution of 4-cyclopropanecarbonyl-9-nitro-3,4,5,6-tetrahydro-2H-1,5-methano-1,4-benzodiazocine (75 g.) in ethanol (600 ml.) and water (300 ml.). The mixture was heated to reflux, then a solution of concentrated hydrochloric acid (45 ml.), ethanol (90 ml.) and water (90 ml.) was added dropwise. Stirring was continued for four hours after the addition was complete. The mixture was allowed to cool somewhat, then sodium bicarbonate (75 g.) was cautiously added, and the mixture was filtered. The filtrate was concentrated nearly to dryness, and the residue was partitioned between water and chloroform. The chloroform layer was washed with brine, dried, treated with charcoal and stripped of chloroform. Two recrystallizations of the tan foam residue from methanol afforded 4-cyclopropanecarbonyl-9-amino-3,4,5,6-tetrahydro-2H-1,5-methano-1,4-benzodiazocine (43 g., m.r. 105°-107° C.), the compound of Formula II wherein Q' is cyclopropanecarbonyl. The product appeared to be a methanol solvate. Recrystallization of part of a similarly prepared product from ethyl acetate afforded product free of solvent (m.r. 142°-144° C.).

D. A mixture of 4-cyclopropanecarbonyl-9-amino-3,4,5,6-tetrahydro-2H-1,5-methano-1,4-benzodiazocine (25.73 g.), lithium aluminum hydride (19 g.) and tetrahydrofuran (1250 ml.) was heated under reflux for about three days. Water (60 ml.) was added with stirring at room temperature, then solid potassium carbonate, potassium hydroxide pellets and charcoal. The mixture was filtered, and the filtrate was concentrated under vacuum. Ethanolic hydrochloric acid was added to a solution of the residual amber glass in ethanol, affording crystalline 4-cyclopropylmethyl-9-amino-3,4,5,6-tetrahydro-2H-1,5-methano-1,4-benzodiazocine dihydrochloride (20.5 g., m.r. 208°-210° C.), which contained water, ethanol and isopropyl alcohol of solvation. Since attempts to recrystallize the product produced glassy solids, an aqueous solution thereof was basified with potassium hydroxide. Crystallization of the resulting oil from ethyl acetate afforded 4-cyclopropylmethyl-9-amino-3,4,5,6-tetrahydro-2H-1,5-methano-1,4-benzodiazocine (11.48 g., m.r. 140°-142° C.), the compound of Formula I wherein Q is cyclopropylmethyl and R and R' are both hydrogens.

E. A solution of ethanesulfonic acid (24 g.) in isopropyl alcohol (80 ml.) was added with warming (40°-50° C.) to a solution of 4-cyclopropylmethyl-9-amino-3,4,5,6-tetrahydro-2H-1,5-methano-1,4-benzodiazocine (26.9 g.) in methanol (120 ml.), affording 4-cyclopropylmethyl-9-amino-3,4,5,6-tetrahydro-2H-1,5-methano-1,4-benzodiazocine diethanesulfonate in two crops (34 g., m.r. 221-225° C.; 14 g., m.r. 211°-219° C.), the second of which was recrystallized from methanol-isopropyl alcohol (10 g., m.r. 221°-224° C.).

F. 4-Cyclopropylmethyl-9-amino-3,4,5,6-tetrahydro-2H-1,5-methano-1,4-benzodiazocine (4.85 g.) and naphthalene-2-sulfonic acid (9 g.) were dissolved in ethanol, and from the solution precipitated 4-cyclopropylmethyl-9-amino-3,4,5,6-tetrahydro-2H-1,5-methano-1,4-benzodiazocine dinaphthalene-2-sulfonate (10.5 g., m.r. 206°-209° C.)

G. In two batches 4-cyclopropylmethyl-9-amino-3,4,5,6-tetrahydro-2H-1,5-methano-1,4-benzodiazocine hydrochloride (combined amount 5.1 g., m.r. 236°-239° C.) precipitated from solutions of the free base (4.9 g., 0.02 mole; 0.1 mole) and equimolar quantities of concentrated hydrochloric acid in ethanol.

H. 4-Cyclopropylmethyl-9-amino-3,4,5,6-tetrahydro-2H-1,5-methano-1,4-benzodiazocine dimethanesulfonate (12.5 g., m.r. 214°-218° C.) precipitated from a solution of the free base (7.2 g.) and methanesulfonic acid (5.8 g.) in isopropyl alcohol.

I. 4-Cyclopropylmethyl-9-amino-3,4,5,6-tetrahydro-2H-1,5-methano-1,4-benzodiazocine 1,5-naphthalenedisulfonate hydrate (5.5 g., m.p. >315° C.) precipitated from an aqueous solution of the free base (4.8 g.) and 1,5-naphthalenedisulfonic acid (75%, 7.7 g.).

J. Levo-3,4,5,6-tetrahydro-2H-1,5-methano-1,4-benzodiazocine was prepared in two crops ($[\alpha]^{25} -199.5°$, $-188.3°$) by forming a salt from the racemic free base 105 g.) (the starting material of part A of this example) and levo-mandelic acid (45.65 g.) and isolating the levo free base from the salt. The two crops were separately cyclopropanecarbonylated by the method of part A of this example, and the combined products ($[\alpha]_D^{25} +30.18°$, 29.12°; 44 g.) were nitrated by the method of part B of this example. The resulting product was purified by high pressure liquid chromatography affording dextro-4-cyclopropanecarbonyl-9-nitro-3,4,5,6-tetrahydro-2H-1,5-methano-1,4-benzodiazocine in two fractions ($[\alpha]_D^{25} +71.9°$, $+73.1°$; 5.75 g.), a solution of which in ethanol (150 ml.) was hydrogenated over palladium on carbon (10%, 0.5 g.) in a mechanical shaker (Parr) for six hours at room temperature. To a solution of the resulting optically isomeric 4-cyclopropanecarbonyl-1-amino-3,4,5,6-tetrahydro-2H-1,5-methano-1,4-benzodiazocine in tetrahydrofuran (25 ml) cooled in an ice-methanol bath was added a solution of diborane in tetrahydrofuran (1 M, 100 ml.). The resulting mixture was stirred under reflux for about three days, acidified with cooling with dilute hydrochloric acid (10 ml. of concentrated hydrochloric acid and 25 ml. of water), heated overnight on the steam bath, basified with sodium hydroxide, and extracted with chloroform. The chloroform extract was dried over potassium carbonate, treated with charcoal, filtered and stripped of solvent. The product was purified by a combination of preparative plate chromatography, column chromatography (alumina) and crystallization from etherpentane-isopropyl acetate, affording levo-4-cyclopropylmethyl-9-3,4,5,6-tetrahydro-2H-1,5-methano-1,4-benzodiazocine (1.5 g., m.r. 94°–95° C., $[\alpha]_D^{25} -80.5°$).

K. Dextro-3,4,5,6-tetrahydro-2H-1,5-methano-1,4-benzodiazocine (13 g., $[\alpha]_D^{25} +218°$) was prepared from the racemic free base (59 g.) (the starting material of part A of this example) by forming salts first with D-tartaric acid and then with dextromandelic acid and isolating the dextro free base from the mandelate salt. The product was cyclopropanecarbonylated by the method of part A of this example, and the resulting product (18.55 g., $[\alpha]_D^{25} -33.6°$) was nitratd by the method of part B of this example. The resulting product was purified by a combination of crystallization from isopropyl acetate (6 g., m.r. 124°–132° C., $[\alpha]_D^{25} -60.0°$), short path column chromarography on inactivated silica gel (10% water) and recrystallization from isopropyl acetate affording levo-4-cyclopropanecarbonyl-9-nitro-3,4,5,6-tetrahydro-2H-1,5-methano-1,4-benzodiazocine (5 g., m.r. 135°–136° C., $[\alpha]_D^{25} -73.4°$). Hydrogenation of this product by the method of part J of this example and reduction of the resulting optically active 4-cyclopropanecarbonyl-1-amino-3,4,5,6-tetrahydro-2H-1,5-methano-1,4-benzodiazocine (5.34 g.) with lithium aluminum hydride by the method of part D of this example followed by a column chromatography of the resulting product on neutral alumina afforded dextro-4-cyclpropylmethyl-9-amino-3,4,5,6-tetrahydro-2H-1,5-methano-1,4-benzodiazocine (520 mg., m.r. 93°–94° C., $[\alpha]_D^{25} +80.7°$).

L. 4-Cyclopropanecarbonyl-3,4,5,6-tetrahydro-2H-1,5-methano-1,4-benzodiazocine (16 g.) was reduced with diborane prepared in situ from sodium borohydride (8.5 g.) and boron trifluoride etherate (42.5 g.) in tetrahydrofuran and isolated first as a hydrochloride salt and finally (from acetone) as the diethanesulfonate salt, affording 4-cyclopropylmethyl-3,4,5,6-tetrahydro-2H-1,5-methano-1,4-benzodiazocine diethanesulfonate (12.0 g., m.r. 167°–169° C.), the diethanesulfate salt of the compound of Formula IX wherein Q is cyclopropylmethyl.

M. Nitration of 4-cyclopropylmethyl-3,4,5,6-tetrahydro-2H-1,5-methano-1,4-benzodiazocine affords 4-cyclopropylmethyl-9-nitro-3,4,5,6-tetrahydro-2H-1,5-methano-1,4-benzodiazocine, the compound of Formula IV wherein Q is cyclopropylmethyl.

N. Reduction of 4-cyclopropylmethyl-9-nitro-3,4,5,6-tetrahydro-2H-1,5-methano-1,4-benzodiazocine affords 4-cyclopropylmethyl-9-amino-3,4,5,6-tetrahydro-2H-1,5-methano-1,4-benzodiazocine, the compound of Formula I wherein Q is cyclopropylmethyl and R and R' are both hydrogens and the product of part D of this example.

EXAMPLE 2

A. A mixture of 3,4,5,6-tetrahydro-2H-1,5-methano-1,4-benzodiazocine (10.5 g.) (the starting material of part A of Example 1), acetic anhydride (25 ml.) and benzene (50 ml.) was heated under reflux for four hours, then concentrated. Methanol was added to the residue, and the mixture was boiled and concentrated. Excess saturated potassium carbonate solution was added to an aqueous solution of the residue, and the mixture was extracted with chloroform. The chloroform extract was dried, filtered and concentrated. Recrystallization of the residue first from ether, then from ether-acetone, then from isopropyl acetate afforded 4-acetyl-3,4,5,6-tetrahydro-2H-1,5-methano-1,4-benzodiazocine (2.25 g., m.r. 105°–106° C.), the compound of Formula VIII.

B. Potassium nitrate (13.14 g.) was added in portions to a solution of 4-acetyl-3,4,5,6-tetrahydro-2H-1,5-methano-1,4-benzodiazocine (26.43 g.) in concentrated sulfuric acid (100 ml.). The mixture was stirred for about three days at room temperature, then quenched in ice (1500 ml.). The resulting mixture was basified with aqueous sodium hydroxide (35%) and extracted with chloroform. The chloroform extract was dried over potassium carbonate, treated with charcoal, filtered and stripped of solvent. Recrystallization of the residue from isopropyl alcohol afforded 4-acetyl-9-nitro-3,4,5,6-tetrahydro-2H-1,5-methano-1,4-benzodiazocine (2.2 g., m.r. 142°–144° C. with resolidification and remelting, m.r. 162°–164° C.), the compound of Formula III wherein Q* is acetyl.

C. A mixture of 4-acetyl-9-nitro-3,4,5,6-tetrahydro-2H-1,5-methano-1,4-benzodiazocine (37.5 g.) and concentrated hydrochloric acid (200 ml.) was heated for four hours on a steam bath, then concentrated. The solid residue was slurried with ethanol (100 ml.) and filtered affording 9-nitro-3,4,5,6-tetrahydro-2H-1,5-methano-1,4-benzodiazocine hydrochloride (30 g., m.r. 255°–260° C.), the hydrochloride salt of the compound of Formula III wherein Q* is hydrogen. The salt was converted with dilute aqueous sodium hydroxide into the free base, a syrupy brown oil (17.5 g.).

D. A mixture of 9-nitro-3,4,5,6-tetrahydro-2H-1,5-methano-1,4-benzodiazocine (17.5 g.), allyl bromide (7.6 ml.), sodium bicarbonate (1 teaspoon) and N,N-dimethylformamide (200 ml.) was stirred overnight at room temperature, then concentrated to dryness. The residue was partitioned between dilute aqueous sodium hydroxide and isopropyl acetate. The isopropyl acetate layer was washed with dilute aqueous sodium hydroxide and brine, filtered and concentrated to dryness. The residue was recrystallized from isopropyl alcohol, and the product was combined with corresponding product (2.3 g.) from a previous a preparation. Ethereal hydrogen chloride was added to a solution of the combined products in ethyl acetate affording 4-allyl-9-nitro-3,4,5,6-tetrahydro-2H-1,5-methano-1,4-benzodiazocine (10 g.), the compound of Formula IV wherein Q is allyl.

E. Iron powder (four 2 g. portions) was added with stirring to a mixture of 4-allyl-9-nitro-3,4,5,6-tetrahydro-2H-1,5-methano-1,4-benzodiazocine (10.0 g.), acetic acid (100 ml.) and water. The mixture was concentrated to dryness, and the residue was partitioned between dilute aqueous sodium hydroxide and chloroform. The chloroform layer was washed with water and concentrated. A solution of the residual tan gum (3 g.) was treated with charcoal and filtered. Ethanesulfonic acid was added to the filtrate, which was then concentrated. The residue was crystallized from isopropyl alcohol affording 4-allyl-9-amino-3,4,5,6-tetrahydro-2H-1,5-methano-1,4-benzodiazocine diethanesulfonate hemihydrate (1 g., m.r. 218°–220° C.), the free base of which is the compound of Formula I wherein Q is allyl and R and R' are both hydrogens.

EXAMPLE 3

A. A mixture of 4-cyclopropanecarbonyl-9-amino-3,4,5,6-tetrahydro-2H-1,5-methano-1,4-benzodiazocine (8 g.) and acetic anhydride (50 ml.) was heated on a steam bath for two hours. Pyridine was added and heating was continued for three hours. The mixture was concentrated to dryness. The residue was partitioned between aqueous base and chloroform. The chloroform layer was dried and concentrated to dryness. Recrystallization of the residue from acetonitrile afforded a product (m.r. 117°–187° C.), which to remove product of diacetylation was warmed with dilute aqueous sodium bicarbonate. Extraction of the resulting mixture with chloroform and concentration of the chloroform extract to dryness afforded 4-cyclopropanecarbonyl-9-acetamido-3,4,5,6-tetrahydro-2H-1,5-methano-1,4-benzodiazocine (about 8 g.), the compound of Formula VI wherein Q' is cyclopropanecarbonyl and R"CONH is acetamido.

B. Borane in tetrahydrofuran (1 M, 250 ml.) was added slowly to a mixture of 4-cycloprapencarbonyl-9-acetamido-3,4,5,6-tetrahydro-2H-1,5-methano-1,4-benzodiazocine (the product of part A of this example) and tetrahydrofuran (200 ml.) and the resulting mixture was heated under reflux. Water was added dropwise, and the tetrahydrofuran was boiled off. The mixture was acidified with hydrochloric acid, heated on a steam bath, basified with sodium hydroxide, and extracted with chloroform. The chloroform extracct was dried, filtered and concentrated to dryness. An ethereal solution of the residue was filtered through magnesium silicate (Florisil), and the filtrate was concentrated to dryness. Ethereal hydrogen chloride was added to a solution of the residue in isopropyl alcohol, affording 4-cyclopropylmethyl-9-ethylamino-3,4,5,6-tetrahydro-2H-1,5-methano-1,4-benzodiazocine dihydrochloride (4.8 g., m.r. 252°–254° C.), the free base of which is the compound of Formula I wherein Q is cyclopropylmethyl, R is hydrogen and R' is ethyl.

C. A mixture of 4-cyclopropylmethyl-9-amino-3,4,5,6-tetrahydro-2H-1,5-methano-1,4-benzodiazocine (3 g.), acetic anhydride (10 ml.) and pyridine (25 ml.) was let stand for two hours at room temperature, then concentrated to dryness. The residue was partitioned between aqueous ammonia and chloroform. The chloroform layer was dried and concentrated to dryness. Recrystallization of the residue from ether afforded 4-cyclopropylmethyl-9-acetamido-3,4,5,6-tetrahydro-2H-1,5-methano-1,4-benzodiazocine (2.5 g., m.r. 131°–132° C.), the compound of Formula V wherein Q is cyclopropylmethyl and R"CONH is acetamido.

D. Reduction of 4-cyclopropylmethyl-9-acetamido-3,4,5,6-tetrahydro-2H-1,5-methano-1,4-benzodiazocine affords 4-cylopropylmethyl-9-ethylamino-3,4,5,6-tetrahydro-2H-1,5-methano-1,4-benzodiazocine, the compound of Formula I wherein Q is cyclopropylmethyl, R is hydrogen and R' is ethyl and the product of part B of this example.

EXAMPLE 4

A. A mixture of 4-cyclopropanecarbonyl-9-amino-3,4,5,6-tetrahydro-2H-1,5-methano-1,4-benzodiazocine (8 g.) and butyric anhydride (70 ml.) was heated on a steam bath overnight, then poured into a mixture of pyridine (500 ml.) and ice-water. The resulting mixture was extracted with chloroform. The chloroform extract was washed with water, dried, treated with charcoal, filtered and concentrated to an oil, which was extracted with boiling cyclohexane, affording as a yellow gum 4-cyclopropanecarbonyl-9-butyramido-3,4,5,6-tetrahydro-2H-1,5-methano-1,4-benzodiazocine, the compound of Formula VI wherein Q' is cyclopropanecarbonyl and R"CONH is butyramido.

B. Borane in tetrahydrofuran (1 M, 250 ml.) was added slowly to a mixture of 4-cyclopropanecarbonyl-9-butyramido-3,4,5,6-tetrahydro-2H-1,5-methano-1,4-benzodiazocine (the product of part A of this example) and tetrahydrofuran (200 ml.) and the resulting mixture was heated under reflux. Water was added dropwise, and the tetrahydrofuran was boiled off. The mixture was acidified with hydrochloric acid, heated on a steam bath, basified with sodium hydroxide, and extracted with chloroform. The chloroform extract was dried, filtered and concentrated to dryness. Crystallization of the resulting orange oil from hexane afforded 4-cyclopropylmethyl-9-butylamino-3,4,5,6-tetrahydro-2H-1,5-methano-1,4-benzodiazocine (4.8 g., m.r. 84°–85° C.), the compound of Formula I wherein Q is cyclopropylmethyl, R is hydrogen and R' is butyl.

EXAMPLE 5

A. Benzoyl chloride (1.153 g.) was added dropwise with ice-cooling to a mixture of 4-cyclopropylmethyl-9-amino-3,4,5,6-tetrahydro-2H-1,5-methano-1,4-benzodiazocine (2.0 g.), triethylamine (1.66 g.) and chloroform. The resulting mixture was stirred overnight at room temperature. Water was added, and the chloroform layer was separated, washed with water, dried, filtered and concentrated. p-Toluenesulfonic acid monohydrate (1.5598 g.) was added to a solution of the residual orange glass (3.0 g.) in methanol, affording 4-cyclopropylmethyl-9-benzamido-3,4,5,6-tetrahydro-2H-1,5-methano-1,4-benzodiazocine p-toluenesulfonate (1.1 g., m.r. 240°–242° C.), the free base of which is the compound of Formula V wherein Q is cyclopropylmethyl and R"CONH is benzamido.

B. Reduction of 4-cyclopropylmethyl-9-benzamido-3,4,5,6-tetrahydro-2H-1,4-methano-1,5-benzodiazocine affords 4-cyclopropylmethyl-9-benzylamino-3,4,5,6-tetrahydro-2H-1,4-methano-1,5-benzodiazocine, the compound of Formula I wherein Q is cyclopropylmethyl, R is hydrogen and R' is benzyl.

Using the preparative methods of the foregoing examples it is contemplated that the following further examples can be prepared.

EXAMPLE 6

Acylation of 3,4,5,6-tetrahydro-2H-1,5-methano-1,4-benzodiazocine (the starting material of part A of Example 1) with propionic anhydride affords 4-propionyl-3,4,5,6-tetrahydro-2H-1,5-methano-1,4-benzodiazocine, the compound of Formula VII wherein Q' is propionyl;

nitration of which affords 4-propionyl-9-nitro-3,4,5,6-tetrahydro-2H-1,5-methano-1,4-benzodiazocine, the compound of Formula III wherein Q' is propionyl; reduction of which affords 4-propionyl-9-amino-3,4,5,6-tetrahydro-2H-1,5-methano-1,4-benzodiazocine, the compound of Formula II wherein Q' is propionyl; reduction of which affords 4-propyl-9-amino-3,4,5,6-tetrahydro-2H-1,5-methano-1,4-benzodiazocine, the compound of Formula I wherein Q is propyl and R and R' are both hydrogens.

EXAMPLE 7

Acylation of 3,4,5,6-tetrahydro-2H-1,5methano-1,4-benzodiazocine (the starting material of part A of Example 1) with isobutyric anhydride affords 4-isobutyryl-3,4,5,6-tetrahydro-2H-1,5-methano-1,4-benzodiazocine, the compound of Formula VII wherein Q' is isobutyryl; nitration of which affords 4-isobutyryl-9-nitro-3,4,5,6-tetrahydro-2H-1,5-methano-1,4-benzodiazocine, the compound of Formula III wherein Q' is isobutyryl; reduction of which affords 4-isobutyryl-9-amino-3,4,5,6-tetrahydro-2H-1,5-methano-1,4-benzodiazocine, the compound of Formula II wherein Q' is isobutyryl; reduction of which affords 4-isobutyl-9-amino-3,4,5,6-tetrahydro-2H-1,5-methano-1,4-benzodiazocine, the compound of Formula I wherein Q is isobutyl and R and R' are both hydrogens.

EXAMPLE 8

Acylation of 3,4,5,6-tetrahydro-2H-1,5-methano-1,4-benzodiazocine (the starting material of part A of Example 1) with pivaloyl chloride affords 4-pivaloyl-3,4,5,6-tetrahydro-2H-1,5-methano-1,4-benzodiazocine, the compound of Formula VII wherein Q' is pivaloyl; nitration of which affords 4-pivaloyl-9-nitro-3,4,5,6-tetrahydro-2H-1,5-methano-1,4-benzodiazocine, the compound of Formula III wherein Q' is pivaloyl; reduction of which affords 4-pivaloyl-9-amino-3,4,5,6-tetrahydro-2H-1,5-methano-1,4-benzodiazocine, the compound of Formula II wherein Q' is pivaloyl; reduction of which affords 4-neopentyl-9-amino-3,4,5,6-tetrahydro-2H-1,5-methano-1,4-benzodiazocine, the compound of Formula I wherein Q is neopentyl and R and R' are both hydrogens.

EXAMPLE 9

Acylation of 3,4,5,6-tetrahydro-2H-1,5-methano-1,4-benzodiazocine (the starting material of part A of Example 1) with 2,2-dichlorocyclopropanecarbonyl chloride affords 4-(2,2-dichlorocyclopropanecarbonyl)-3,4,5,6-tetrahydro-2H-1,5-methano-1,4-benzodiazocine, the compound of Formula VII wherein Q' is 2,2-dichloropropanecarbonyl; nitration of which affords 4-(2,2-dichlorocyclopropanecarbonyl)-9-nitro-3,4,5,6-tetrahydro-2H-1,5-methano-1,4-benzodiazocine, the compound of Formula III wherein Q' is 2,2-dichlorocyclopropanecarbonyl; reduction of which affords 4-(2,2-dichlorocyclopropanecarbonyl)-9-amino-3,4,5,6-tetrahydro-2H-1,5-methano-1,4-benzodiazocine, the compound of Formula II wherein Q' is 2,2-dichlorocyclopropanecarbonyl; reduction of which affords 4-((2,2-dichlorocyclopropyl)methyl)-9-amino-3,4,5,6-tetrahydro-2H-1,5-methano-1,4-benzodiazocine, the compound of Formula I wherein Q is (2,2-dichlorocyclopropyl)methyl and R and R' are both hydrogens.

EXAMPLE 10

Alkylation of 9-nitro-3,4,5,6-tetrahydro-2H-1,5-methano-1,4-benzodiazocine with 2-methyl-2-propenyl bromide affords 4-(2-methyl-2-propenyl)-9-nitro-3,4,5,6-tetrahydro-2H-1,5-methano-1,4-benzodiazocine, the compound of Formula IV wherein Q is 2-methyl-2-propenyl; reduction of which affords 4-(2-methyl-2-propenyl)-9-amino-3,4,5,6-tetrahydro-2H-1,5-methano-1,4-benzodiazocine, the compound of Formula I wherein Q is 2-methyl-2-propenyl and R and R' are both hydrogens.

EXAMPLE 11

Alkylation of 9-nitro-3,4,5,6-tetrahydro-2H-1,5-methano-1,4-benzodiazocine with 2-chloro-2-propenyl bromide affords 4-(2-chloro-2-propenyl)-9-nitro-3,4,5,6-tetrahydro-2H-1,5-methano-1,4-benzodiazocine, the compound of Formula IV wherein Q is 2-chloro-2-propenyl; reduction of which affords 4-(2-chloro-2-propenyl)-9-amino-3,4,5,6-tetrahydro-2H-1,5-methano-1,4-benzodiazocine, the compound of Formula I wherein Q is 2-chloro-2-propenyl and R and R' are both hydrogens.

EXAMPLE 12

Alkylation of 9-nitro-3,4,5,6-tetrahydro-2H-1,5-methano-1,4-benzodiazocine with cis-3-chloro-2-propenyl bromide affords 4-(cis-3-chloro-2-propenyl)-9-nitro-3,4,5,6-tetrahydro-2H-1,5-methano-1,4-benzodiazocine, the compound of Formula IV wherein Q is cis-3-chloro-2-propenyl; reduction of which affords 4-(cis-3-chloro-2-propenyl)-9-amino-3,4,5,6-tetrahydro-2H-1,5-methano-1,4-benzodiazocine, the compound of Formula I wherein Q is cis-3-chloro-2-propenyl and R and R' are both hydrogens.

EXAMPLE 13

Alkylation of 9-nitro-3,4,5,6-tetrahydro-2H-1,5-methano-1,4-benzodiazocine with cis-3-chloro-2-butenyl bromide affords 4-(cis-3-chloro-2-butenyl)-9-nitro-3,4,5,6-tetrahydro-2H-1,5-methano-1,4-benzodiazocine, the compound of Formula IV wherein Q is cis-3-chloro-2-butenyl; reduction of which affords 4-(cis-3-chloro-2-butenyl)-9-amino-3,4,5,6-tetrahydro-2H-1,5-methano-1,4-benzodiazocine, the compound of Formula I wherein Q is cis-3-chloro-2-butenyl and R and R' are both hydrogens.

EXAMPLE 14

Alkylation of 9-nitro-3,4,5,6-tetrahydro-2H-1,5-methano-1,4-benzodiazocine with trans-3-chloro-2-butenyl bromide affords 4-(trans-3-chloro-2-butenyl)-9-nitro-3,4,5,6-tetrahydro-2H-1,5-methano-1,4-benzodiazocine, the compound of Formula IV wherein Q is trans-3-chloro-2-butenyl; reduction of which affords 4-(trans-3-chloro-2-butenyl)-9-amino-3,4,5,6-tetrahydro-2H-1,5-methano-1,4-benzodiazocine, the compound of Formula I wherein Q is trans-3-chloro-2-butenyl and R and R' are both hydrogens.

EXAMPLE 15

Alkylation of 9-nitro-3,4,5,6-tetrahydro-2H-1,5-methano-1,4-benzodiazocine with propargyl bromide affords 4-propargyl-9-nitro-3,4,5,6-tetrahydro-2H-1,5-methano-1,4-benzodiazocine, the compound of Formula IV wherein Q is propargyl; reduction of which affords 4-propargyl-9-amino-3,4,5,6-tetrahydro-2H-1,5- methano-1,4-benzodiazocine, the compound of Formula I wherein Q is propargyl and R and R' are both hydrogens.

EXAMPLE 16

Dimethylation of 4-cyclopropylmethyl-9-amino-3,4,5,6-tetrahydro-2H-1,5-methano-1,4-benzodiazocine affords 4-cyclopropylmethyl-9-dimethylamino-3,4,5,6-tetrahydro-2H-1,5-methano-1,4-benzodiazocine, the compound of Formula I wherein Q is cyclopropylmethyl and R and R' are both methyls.

EXAMPLE 17

Acylation of 4-cyclopropylmethyl-9-amino-3,4,5,6-tetrahydro-2H-1,5-methano-1,4-benzodiazocine with formic-acetic anhydride affords 4-cyclopropylmethyl-9-formamido-3,4,5,6-tetrahydro-2H-1,5-methano-1,4-benzodiazocine, the compound of Formula V wherein Q is cyclopropylmethyl and R"CONH is formamido; reduction of which affords 4-cyclopropylmethyl-9-methylamino-3,4,5,6-tetrahydro-1,5-methano-1,4-benzodiazocine, the compound of Formula I wherein Q is cyclopropylmethyl, R is hydrogen and R' is methyl.

EXAMPLE 18

Acylation of 4-cyclopropylmethyl-9-amino-3,4,5,6-tetrahydro-2H-1,5-methano-1,4-benzodiazocine with propionic anhydride affords 4-cyclopropylmethyl-9-propionamido-3,4,5,6-tetrahydro-2H-1,5-methano-1,4-benzodiazocine, the compound of Formula V wherein Q is cyclopropylmethyl and R"CONH is propionamido; reduction of which affords 4-cyclopropylmethyl-9-propylamino-3,4,5,6-tetrahydro-1,5-methano-1,4-benzodiazocine, the compound of Formula I wherein Q is cyclopropylmethyl, R is hydrogen and R' is propyl.

EXAMPLE 19

Acylation of 4-cyclopropylmethyl-9-amino-3,4,5,6-tetrahydro-2H-1,5-methano-1,4-benzodiazocine with isobutyric anhydride affords 4-cyclopropylmethyl-9-isobutyramido-3,4,5,6-tetrahydro-2H-1,5-methano-1,4-benzodiazocine, the compound of Formula V wherein Q is cyclopropylmethyl and R"CONH is isobutyramido-3,4,5,6-tetrahydro-1,5-methano-1,4-benzodiazocine, the compound of Formula I wherein Q is cyclopropylmethyl, R is hydrogen and R' is isobutyl.

Biological Test Results

As stated above the compounds of Formula I are useful as strong analgesics. This conclusion is supported by results of the following presumptive tests of analgesia.

Anti-acetylcholine Writhing Test

An intraperitoneal injection of acetylcholine (3.2 mg./kg.) causes mice to exhibit a response consisting of abdominal constriction, and sometimes twisting, followed by extension of the hind limbs. This response has been called writhing. Animals are pretreated with test compounds (20 minutes for both subcutaneous and oral routes) and observed for two minutes immediately following the administration of acetylcholine. Mice not responding during the two-minute observation period are scored protected while those responding one or more times are scored not protected. Test compounds are screened at doses of 75 and 25 mg./kg. subcutaneously or 150 and 50 mg./kg. orally. The standard injection volume for test compounds is 10 ml./kg. ED50 values for active compounds are estimated by probit analysis of quantal scores for 4 or more dosage levels using 15 animals per dose. Vehicle-pretreated control animals are tested concurrently with each run of 15 experimental animals. The products of parts D, E, J and K of Example 1, part E of Example 2, part B of Example 3 and part B of Example 4 were tested and were active in this test as shown by the following results:

| Product Example | ED50 Expressed in Mg./Kg. of Free Base (95% Confidence Limits) | |
|---|---|---|
| | Subcutaneous | Oral |
| 1D | 3.2 (2.0–4.8) | 5.9 (3.9–8.7) |
| 1E | 3.7 (2.6–5.2) | a |
| 1J | 40 (b) | a |
| 1K | 1.0 (0.62–2.0) | a |
| 2E | 30 (c) | a |
| 3B | 3.8 (2.8–5.0) | a |
| 4B | 1.6 (1.0–2.8) | a |

(a) not tested
(b) 67% response at 75 mg./kg. (highest dose tested)
(c) estimated from three dosage levels

Anti-phenylquinone Writhing Test

This test is used to supplement the anti-acetylcholine writhing test. The ability of compounds to prevent phenyl-p-quinone (phenylquinone)-induced writhing in mice is determined in this test. An intraperitoneal injection of phenylquinone, 3.0 mg./kg., causes mice to exhibit the same writhing response as does acetylcholine as described above. Animals are pretreated with test compounds (15 minutes for subcutaneous route, 30 minutes for oral route) and observed for three one-minute intervals during the 5–14 minutes following administration. Mice responding fewer than three times during the three one-minute observation periods are scored protected while those responding three or more times are scored not protected. Test compounds are screened using 10–14 animals per treatment, usually at doses of 75–100 mg./kg. subcutaneously or 150–200 mg./kg. orally. The standard injection volume for test compounds is 10 ml./kg. ED50 values for active compounds are estimated by probit analysis of quantal scores for 3–5 dosage levels using 14–30 animals per dose. Vehicle-pretreated control animals are tested daily. Only the product of part D of Example 1 was tested in this test. It showed the following results:

| Product of Example | ED50 Expressed in Mg./Kg. of Free Base (95% Confidence Limits) | |
|---|---|---|
| | Subcutaneous | Oral |
| 1D | 1.8 (1.1–2.9) | 5.7 (4.5–7.1) |

Anti-bradykinin Test

This is a confirmatory evaluation of analgesic activity. Rats prepared surgically under ether anesthesia with an indwelling intra-carotid cannula exhibit a response to bradykinin injections consisting of ipsilateral head rotation and front paw flexion. The threshold dose of bradykinin required for production of the response is determined for each animal, and is readministered at fixed intervals during a two-hour period following the subcutaneous or oral administration of test compounds. In the control response marked rotation of the head and flexion of the forepaw are each scored +2, for a total response score (TRS) of +4. For post-medication scoring any decrease in head rotation or paw flexion from control is each scored +1, rather than 30 2, while no movement of either the head or paw is each scored 0. Therefore, the TRS following any bradykinin challenge can vary from 0 to 4. Animals whose TRSs are 0—0, 0—+1 or +1-0 after any two consecutive bradykinin challenges during the two-hour post-medication period are scored protected. Compounds are screened using 5 animals per treatment, usually at 100 mg./kg. subcutaneously or 200 mg./kg. orally. The standard injection volume for test compounds is 2 ml./kg. for both subcutaneous and oral medication. ED50 values of active compounds are estimated by probit analysis of quantal scores from 4 or more dosage levels using 5 animals per dose. In addition the average TRSs obtained at each test interval with each treatment are plotted to permit examination of time-effect relationships and to provide a rough expression of drug effect using graded data. A vehicle-pretreated control animal is tested daily. An aqueous bradykinin formulation is diluted with saline to the proper concentrations for determination of threshold doses for producing the response. All bradykinin injections are made at a constant volume of 0.2 ml. per rat. The products of parts D and E of Example 1, part B of Example 3 and part B of Example 4 were tested in this test and showed the following results.

| Product of Example | ED50 Expressed in Mg./Kg. of Free Base (95% Confidence Limits) | |
| --- | --- | --- |
| | Subcutaneous | Oral |
| 1D | 2.6 (1.5–4.1) | 5.4 (0.005–7.3) |
| 1E | a | 4.2 (2.1–6.2) |
| 3B | 3.4 (1.6–6.1) | a |
| 4B | 2.9 (1.0–6.0) | a |

EDTA Antinociceptive Test

This is also a confirmatory evaluation of analgesic activity. The test animal is the guinea pig. A threshold intradermal dose of ethylenediaminetetraacetic acid (EDTA) which can reproducibly elicit a cumulative response score of 12–18 discrete episodes of jumping, rearing, running, vocalization and biting or scratching at the site of injection within 40 seconds after challenge is determined for each animal. Thirty minutes after the administration of saline or test compound to 6–7 animals per dose, each animal is again challenged with its own threshold dose of EDTA. An effective drug dose is considered to be one which reduces the response score to 6 or less. The product of part D of Example 1 was tested in this test and had a subcutaneously effective dose of 1.25 mg./kg.

Some of the compounds of Formula I are useful as narcotic antagonists as shown by the following tail-flick test. The tail-flick test is also a test for analgesics of the narcotic type.

Tail-flick Agonist Test

Rats normally respond to a thermal stimulus applied to the tail by flicking their tails out from under the heat source. The intensity of the stimulus utilized is one which produces control response-times (CRT) of 2–4 seconds. Experimental response-time (ERT) are determined 30 minutes after subcutaneous injections and 60 minutes after oral medications. The stimulus is terminated if animals did not respond after an exposure of 20 seconds. Therefore, the maximum possible increase (MPI) in response-time for any given animal is 20 minus the CRT. The average percent effect, or percent of the maximum possible increase (% MPI) obtained after any given test compound treatment is calculated by the formula $$\% \ MPI = \frac{\text{Average } ERT - \text{Average } CRT}{20 - \text{Average } CRT} \times 100.$$

Test compounds are screened using 6 animals per treatment usually at 120 mg./kg. subcutaneously or 200 mg./kg. orally. The standard injection volume for test compounds is 1.0 ml./kg. subcutaneously and 10 ml./kg. orally. ED50 values of active compounds are obtained by the Miller and Tainter [Proc. Soc. Exptl. Biol., N.Y., 57:261 (1944)] method of probit analysis of data from at least 3 dosage levels using 18 animals per treatment. The products of Examples 1D, 1E, 3B and 4B were tested in this test. All were at most inactive or questionably active at doses up to 120 mg./kg. subcutaneously, and none showed sufficient separation of agonist and toxic effects to permit calculation of an ED50 value.

Tail-flick Antagonist Test

The rat tail-flick test is also used to determine whether compounds have narcotic antagonist activity. Animals are pretreated (10 minutes for subcutaneous route, 20 minutes for oral route) with test compounds and are then given subcutaneously a standard ED80 dose of phenazocine (as the hydrobromide, 0.5 mg./kg.) or meperidine (as the hydrochloride, 50 mg./kg.) or a standard ED90 dose of morphine (as the sulfate, 15 mg./kg.). Active compounds reduce, in a dose-dependent manner, and can completely block, the agonist effect of all narcotics. The average percent antagonist effect produced by any given treatment is calculated by the formula $$\% \ \text{antagonism} = 100 - \frac{\% \ MPI \ \text{of narcotic} + \text{test drug}}{0.80}$$

Test compounds are screened using 6 animals per treatment, usually at 80 mg./kg. subcutaneously or 200 mg./kg. orally. The standard injection volume for test compounds is 1.0 ml./kg. subcutaneously and 10 ml./kg. orally. AD50 values of active compounds are obtained from Litchfield-Wilcoxon [J. Pharm. Exptl. Therap., 96:99 (1944)] plots of data from at least 3 dosage levels using 18 animals per treatment. Subcutaneously against phenazocine, the product of part J of Example 1 showed a 10% response at 1 mg./kg., a 6% response at 10 mg./kg. and a 25% response at 80 mg./kg., and the product of part B of Example 4 showed a 6% response at 1 mg./kg., a 0% response at 10 mg./kg. and a 34% response at 20 mg./kg. with toxic effects at 20 mg./kg. Subcutaneous AD50 values against phenazocine expressed as mg./kg. of free base were obtained for the products of part K of Example 1, part E of Example 2 and part B of Example 3:

| Product of Example | AD50 (95% Confidence Limits) |
| --- | --- |
| 1K | 0.31 (0.15–0.60) |
| 2E | 1.6 (1.0–2.6) |
| 3B | 4.4 (2.9–6.6) |

AD50 values against all three narcotics expressed as mg./kg. of free base were obtained for the products of part D (subcutaneously) and part E (orally) of Example 1:

| Narcotic | AD50 (95% Confidence Limits) | |
|---|---|---|
| | Subcutaneous | Oral |
| phenazocine | 1.6 (1.0–2.6) | 3.5 (2.3–5.2) |
| meperidine | 3.3 (2.1–5.3) | 4.8 (3.5–6.5) |
| morphine | 8.6 (5.7–13) | 13 (8.6–19) |

Comparative Biological Test Results

By comparison in three of the foregoing tests the product of part D of Example 1 having the structural formula Formula I* was shown to be four to ten times more potent than the compound of above-cited Gubitz U.S. Pat. No. 3,472,852 differing by lack of 9-amino and having the structural formula Formula A* as shown by the following results.

| | ED50 or AD50 Expressed in Mg./Kg. of Free Base (95% Confidence Limits) | |
|---|---|---|
| Test | Compound of Formula I* | Compound of Formula A* |
| Anti-acetylcholine Writhing test | 3.2 (2.0–4.8)[a] | 12 (7.4–20)[a] |
| Anti-acetylcholine Writhing Test | 5.9 (3.9–8.7)[b] | 32 (21–47)[b] |
| Anti-bradykinin Test | 2.6 (1.5–4.1)[a] | 21 (8.8–46)[a] |
| Tail-flick Antagonist Test[c] | 1.6 (1.0–2.6)[a] | 34 (20–58)[a] |

[a]Subcutaneous
[b]Oral
[c]Against phenazocine

The Compositions

The compounds of Formula I can be administered orally and parenterally. For these routes of administration appropriate conventional pharmaceutical vehicles and adjuncts can be formulated with the compounds of Formula I to prepare liquid and solid dosage forms as solutions, suspensions, emulsions, capsules and tablets.

PATENTABILITY STATEMENT

The invention described above and claimed below is new and useful, and in view of the prior art and the comparative biological test results shown above would not have been obvious to one of ordinary skill in the art at the time it was made, and is therefore patentable.

I claim:

1. 4-Q-9-RR′N-3,4,5,6-tetrahydro-2H-1,5-methano-1,4-benzodiazocine having the structural formula wherein Q is propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl; and R and R′ are both hydrogens or both methyls; or R is hydrogen and R′ is methyl, ethyl, propyl, butyl, isobutyl or benzyl; or an acid addition salt thereof.

2. A compound according to claim 1 wherein R and R′ are both hydrogens or an acid addition salt thereof.

3. A compound according to claim 2 wherein Q is cyclopropylmethyl or an acid addition salt thereof.

4. A compound according to claim 2 wherein Q is allyl or an acid addition salt thereof.

5. A compound according to claim 1 wherein Q is cyclopropylmethyl or an acid addition salt thereof.

6. A compound according to claim 5 wherein R is hydrogen and R′ is ethyl or an acid addition salt thereof.

7. A compound according to claim 5 wherein R is hydrogen and R′ is butyl or an acid addition salt thereof.

8. 4-Q′-9-amino-3,4,5,6-tetrahydro-2H-1,5-methano-1,4-benzodiazocine having the structural formula wherein Q′ is propionyl, isobutyryl, pivalolyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl; or an acid addition salt thereof.

9. A compound according to claim 8 wherein Q′ is cyclopropanecarbonyl or an acid addition salt thereof.

10. 4-Q*-9-nitro-3,4,5,6-tetrahydro-2H-1,5-methano-1,4-benzodiazocine having the structural formula wherein Q* is hydrogen, acetyl or Q′, wherein Q′ is propyl, isobutyryl, pivalolyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;

or an acid addition salt thereof.

11. A compound according to claim 10 wherein Q* is acetyl or an acid addition salt thereof.

12. A compound according to claim 10 wherein Q* is Q' and Q' is cyclopropanecarbonyl or an acid addition salt thereof.

13. 4-Q-9-nitro-3,4,5,6-tetrahydro-2H-1,5-methano-1,4-benzodiazocine having the structural formula

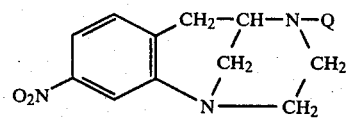

wherein

Q is propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;

or an acid addition salt thereof.

14. 4-Q-9-R"CONH—3,4,5,6-tetrahydro-2H-1,5-methano-1,4-benzodiazocine having the structural formula

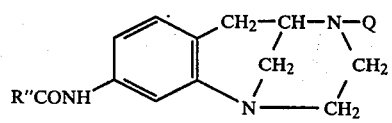

wherein

Q is propyl, isobutyl, neopentyl, alkyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;

R"CONH is formamido, acetamido, propionamido, butyramido, isobutyramido or benzamido; or an acid addition salt thereof.

15. A compound according to claim 14 wherein Q is cyclopropylmethyl or an acid addition salt thereof.

16. A compound according to claim 15 wherein R"CONH is acetamido or an acid addition salt thereof.

17. A compound according to claim 15 wherein R"CONH is benzamido or an acid addition salt thereof.

18. 4-Q'-9-R"CONH-3,4,5,6-tetrahydro-2H-1,5-methano-1,4-benzodiazocine having the structural formula

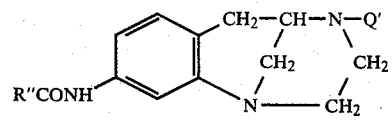

wherein

Q' is propionyl, isobutyryl, pivalolyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl; and R"CONH is formamido, acetamido, propionamido, butyramido, isobutyramido or benzamido.

19. The process of producing analgesia in a mammal in pain which comprises administering to the mammal an analgesically effective amount of a compound according to claim 1 or a pharmaceutically acceptable acid addition salt thereof in a pharmaceutically acceptable carrier.

20. An analgesic pharmaceutical composition in solid or liquid dosage form for oral or parenteral administration consisting essentially of an analgesically effective amount of a compound according to claim 1 or a pharmaceutically acceptable acid addition salt thereof and a pharmaceutically acceptable vehicle.

* * * * *